US005379655A

United States Patent [19]

Yeakle

[11] Patent Number: 5,379,655

[45] Date of Patent: Jan. 10, 1995

[54] OBSTRUCTION SENSING GUARD FOR VERTICALLY MOVING TABLE

[75] Inventor: William H. Yeakle, Angola, Ind.

[73] Assignee: Vestil Manufacturing Company, Angola, Ind.

[21] Appl. No.: 139,547

[22] Filed: Oct. 20, 1993

[51] Int. Cl.⁶ .......................... G01N 33/00; B66B 9/04

[52] U.S. Cl. .................................... 73/865.7; 187/269

[58] Field of Search ........................ 73/865.7; 192/133; 100/256, 281; 187/18, 40, 41, 98, DIG. 1, 101, 112, 134, 136; 414/495, 674; 74/16; 144/286.2

[56] References Cited

U.S. PATENT DOCUMENTS

| | | | |
|---|---|---|---|
| 4,091,906 | 5/1978 | Clarke et al. . | |
| 4,362,196 | 12/1982 | Ferdinand et al. | 144/286 R |
| 4,392,771 | 7/1983 | Smalley . | |
| 4,556,129 | 12/1985 | Martin . | |
| 4,596,412 | 6/1986 | Everett et al. . | |
| 4,724,554 | 2/1988 | Kowalski et al. | 5/610 |

FOREIGN PATENT DOCUMENTS

| | | | |
|---|---|---|---|
| 383944 | 3/1908 | France . | |
| 1756318 | 4/1970 | Germany . | |
| 1756343 | 4/1970 | Germany . | |
| 2360284 | 6/1975 | Germany | 414/674 |

OTHER PUBLICATIONS

Vestil Manufacturing Company, Scissor Tables advertisement/bulletin sheet.

*Primary Examiner*—Hezron E. Williams
*Assistant Examiner*—Daniel S. Larkin
*Attorney, Agent, or Firm*—George Pappas

[57] ABSTRACT

An obstruction sensing guard for use on a vertically-moving lift table for sensing an obstruction and stopping movement of the lift table in response thereto. The guard includes a sensor bar extending vertically below and generally along the table outer perimeter. The sensor bar is hung below the table via flexible connections that allow both horizontal and vertical movement of the sensor bar with respect to the table. The sensor bar is easily assembled with connecting boots at each corner and elongate beams extending therebetween and connected to the boots. Electric contact switches are provided on the sensor bar and are actuated when the sensor bar is moved. The contact switches are retained on the sensor bar with a switch clip that frictionally engages the sensor bar.

20 Claims, 2 Drawing Sheets

OBSTRUCTION SENSING GUARD FOR VERTICALLY MOVING TABLE

TECHNICAL FIELD

The present invention relates to the technical field of lift tables wherein the table surface is selectively raised and lowered for moving components and other items placed thereon to a desired height. More specifically, the present invention relates to an obstruction sensing guard for a vertically moving table for sensing an obstruction when the table is being lowered and for interrupting further movement of the table in response thereto.

BACKGROUND OF THE INVENTION

Lift tables are presently commonly used in many industries for placing various components and other items on the table surface and selectively automatically raising and lowering the table and components to a desired height. Typically, the lift tables include a base, a table top and a raising and lowering mechanism therebetween. The raising and lowering mechanism can be vertically situated hydraulic cylinders, scissor arms actuated by hydraulic cylinders, screw mechanisms etc. The mechanisms are controlled by the operator either near or remotely from the lift table.

The table and components that may be carried thereon are typically quite heavy and as a consequence, while the table is being lowered, it is possible for something that may be in the table's travel path to be damaged. It is also possible for the operator to be injured if, for example, his leg or toes are accidentally within the table traveling path. In this regard, and so as to prevent such damage and injuries from occurring, obstruction sensing guards commonly known as toe guards have been incorporated with lift tables. These guards are typically located near and below the perimeter of the table and are adapted to interrupt further movement of the table in the event that the sensor guard experiences an obstruction. One such type of sensing guard includes a sensor bar underneath and generally along the perimeter of the table and the sensor bar is hung on the table via bolts or other sliding means extending through a bore. This allows vertical movement of the sensor bar in the event of an obstruction. An electrical switch is provided between the sensor bar and the table so that upon vertical movement of the sensor bar, the switch is tripped for providing the necessary signal to the control circuit causing the table to stop from moving further. However, if the sensor guard is also exposed to a horizontal force, it is possible for the bolts or other sliding mechanism to bind within the bores preventing movement of the guard vertically upwardly and also preventing tripping of the contact switch.

In addition to the foregoing drawback, prior obstruction sensing guards are relatively time-consuming and expensive to manufacture. For example, the sensor bar as currently manufactured requires assembly by welding the various elongate lengths together around the table and thereafter lifting the toe guard and hanging the same in place via the bolts and bore configuration. As can be appreciated, this welding process requires substantial expertise and experience and, as a consequence, increases the overall cost of manufacturing.

Accordingly, a need exists for an obstruction sensing guard for vertically moving tables that will not bind in the event that both vertical and horizontal forces are experienced and which is generally easy and inexpensive to manufacture.

SUMMARY OF THE INVENTION

It is the principal object of the present invention to overcome the above-discussed disadvantages associated with prior obstruction sensing guards or toe guards for vertically moving tables.

The present invention overcomes the disadvantages associated with prior obstruction sensing guards by hanging the sensor bar below the vertically moving table in a manner whereby the sensor bar is allowed to move both horizontally and vertically with respect to the table and in a manner whereby a horizontal force thereon cannot cause the sensor bar to bind preventing vertical movement. The mechanism for accomplishing this includes a plurality of connections between the sensor bar and the table and, preferably, these connections are located at each corner of the table and sensor bar. Each of the connections include a flexible elongate member with a first end connected to the table and a second end connected to the sensor bar. Preferably, the flexible connector is made of a plurality of chained links intermediate eyelets connected to the corners of the table and sensor bar. The sensor bar, thus, is hanging below the table generally below the perimeter thereof. Any horizontal force experienced by the sensor bar merely causes it to move both horizontally and vertically upwardly.

A contact switch is mounted or retained on the sensor bar in manner whereby movement of the sensor bar causes the switch to come in contact with the table. The contact switch is wired into the control circuit such that actuation of the contact switch causes the table to stop further movement. A generally U-shaped switch clip is provided and has two walls sandwiching the sensor bar and a pocket wherein the contact switch is frictionally retained. The switch clip walls frictionally engage the sensor bar for retaining their position. The switch clip provides versatility and allows mounting the contact switch substantially anywhere along the sensor bar. Additionally, the switch clip is made by stamping and bending processes and is, therefore, relatively inexpensive to manufacture. This, combined with the ease of assembly on the sensor bar, provide for overall decreased manufacturing costs.

The sensor bar includes connecting boots at each table corner and elongate beams extending therebetween and connected to the boots. The rubber boots are made by an injection molding process and are formed with beam receiving channels for frictionally receiving an end portion of the beams. Accordingly, assembly merely requires cutting the beams to length and frictionally inserting the ends thereof within the beam receiving channels of the connecting boots. By varying the lengths of the beams, different size sensor bars can easily be assembled and manufactured for different size tables.

The connecting boots further include a hole used for connecting the sensor bar to the table. An eyelet member extends through the hole and is affixed to the boot and a chain link extends through the eyelet member and through a second eyelet which is connected to the underside of the table. As can be appreciated, this provides for an easily assemblable sensing guard which is both versatile and relatively inexpensive.

In one form thereof, the present invention is directed to an obstruction sensing guard for a vertically moving table having an outer perimeter. The obstruction sensing guard includes a sensor bar extending generally along and vertically below the table outer perimeter. A mechanism is provided for hanging the sensor bar below the table and for allowing both horizontal and vertical movement of the sensor bar with respect to the table. A mechanism is also provided for sensing movement of the sensor bar with respect to the table and interrupting movement of the table in response thereto.

In one form thereof, the present invention is directed to an obstruction sensing guard for a generally horizontally disposed vertically moving quadrangle-shaped table having four corners and an outer perimeter. The obstruction sensing guard includes a sensor bar extending generally along and vertically below the table outer perimeter. The sensor bar includes connecting boots at each table corner and elongate beams extending therebetween and connected to the boots. A mechanism is provided for hanging the sensor bar below the table and for allowing movement of the sensor bar with respect to the table. A mechanism is also provided for sensing movement of the sensor bar with respect to the table and interrupting movement of the table in response thereto.

In one form thereof, the present invention is directed to an obstruction sensing guard for a vertically moving table having an outer perimeter. The obstruction sensing guard includes a sensor bar extending generally along and vertically below the table outer perimeter. A mechanism is provided for hanging the sensor bar below the table and for allowing movement of the sensor bar with respect to the table. An electronic contact switch is provided and is adapted to interrupt movement of the table when actuated. A mechanism is also provided for engaging the sensor bar and retaining the contact switch thereon whereby the switch is caused to be actuated by contacting the table when the sensor bar moves toward the table.

BRIEF DESCRIPTION OF THE DRAWINGS

The above mentioned and other features and objects of this invention and the manner of obtaining them will become more apparent and the invention itself will be better understood by reference to the follow description of embodiments of the invention taken in conjunction with the accompanying drawings wherein.

Corresponding reference characters indicate corresponding parts throughout the several views of the drawings.

The exemplifications set out herein illustrate preferred embodiments of the invention in one form thereof and such exemplifications are not to be construed as limiting the scope of the disclosure or the scope of the invention in any manner.

DETAILED DESCRIPTION OF SPECIFIC EMBODIMENTS

Figure 1:
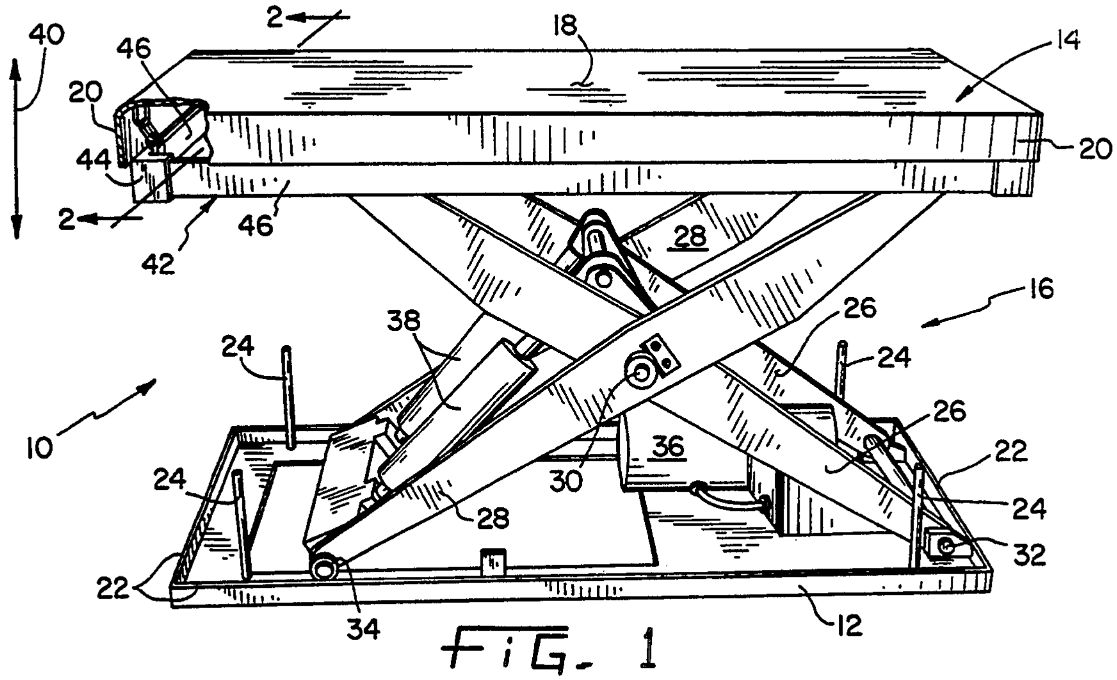
FIG. 1 is a perspective view of a scissor lift table incorporating an obstruction sensing guard according to the present invention.

Referring initially to FIG. 1, a lift table incorporating an obstruction sensing guard according to the present invention is generally designated by the numeral 10. Lift table 10 includes a base 12, table 14 and scissor lift mechanism 16. Table 14 has a top 18 and an apron 20 therearound at the perimeter of table top 18. Base 12 includes upright portions 22 for providing stability and includes vertically situated rods 24 for contacting table top 18 and limiting the downward travel thereof.

Scissor lift mechanism 16 includes lift arms 26 and 28 pivotally connected with a central pin 30. Lift arms 26 are pivotally connected via pin 32 to base 12 whereas arms 28 are pivotally connected to table 14 (not shown). At the end opposite the pivotal connections between the arms 26 and 28 and base 12 and table 14 respectively, arms 26 and 28 are provided with roller bearings 34 for sliding and rolling engagement with the base 12 and with the table (not shown). A hydraulic pump 36 and a control circuit (not shown) is provided for selectively actuating hydraulic cylinders 38 and causing arms 26 and 28 to selectively pivot about central pin 30. Thus, by controlling the actuation of hydraulic cylinders 38, table 14 is selectively caused to move vertically up and down as indicated by the arrows 40. It is noted that the scissor lift mechanism as shown and described hereinabove is already known and widely used in the industry as a means of selectively lifting a table and contents or items that may be placed thereon. Other lift mechanisms are also currently known and are available for this purpose.

Figure 2:
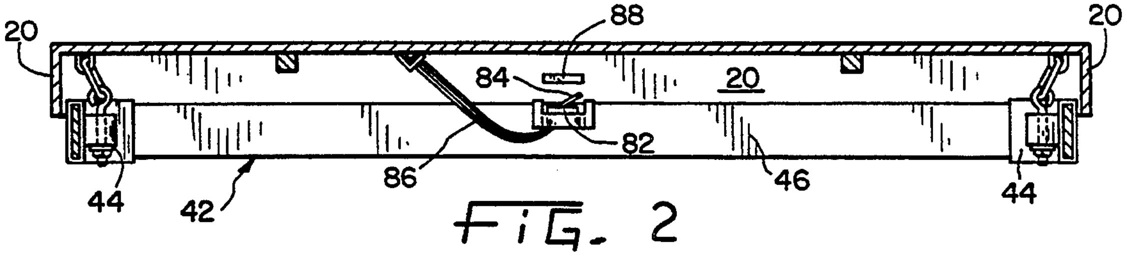
FIG. 2 is a cross sectional view of the table and obstruction sensing guard shown in FIG. 1 and taken along line 2—2.

Lift table 10 is equipped with an obstruction sensing guard so that if an object is in the path of table 14 as it is traveling downwardly, the obstruction can be sensed and a signal sent to the control circuit to stop hydraulic cylinders 38 and to also therefore stop further movement of arms 26 and 28. The obstruction sensing guard includes a sensor bar generally indicated by the numeral 42 and which is located generally along and vertically below the outer perimeter of table 14. Preferably, as shown in FIGS. 1 and 2, sensor bar 42 is just inside of apron 20 below table top 18.

Figure 3:
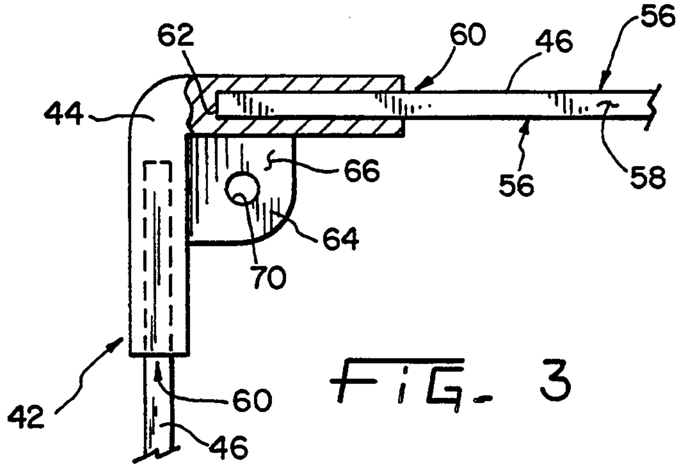
FIG. 3 is a top plan view of a connecting boot and beams of a sensor bar corner according to the present invention.
Figure 4:
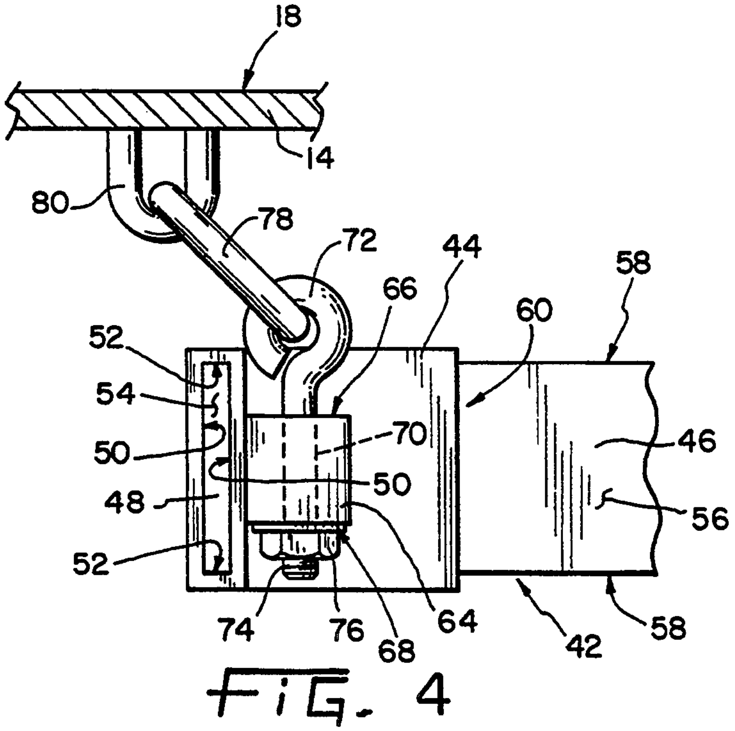
FIG. 4 is a side elevational view of a sensor bar corner connection to the underside of a table according to the present invention.

Sensor bar 42 is preferably constructed as shown including connecting boots 44 at each corner and elongate beams 46 extending therebetween and connected to boots 44. More specifically, boots 44 are made of hard rubber by an injection molding process and are formed with channels or openings 48. Channels 48 are generally rectangular in cross section having longer side walls 50 and short side walls 52. Channels 48 terminate at a back wall 54. As best shown in FIGS. 3 and 4, channels 48 are formed in boots 44 so as to be at a 90 degree angle from each other for forming a typical table corner.

Beams 46 are adapted to be received within channels 48 and are, thus, also rectangularly-shaped having longer side walls 56 and short walls 58. For assembly, beams 46 are cut to length as needed for a particular lift table side and the end portions 60 thereof are frictionally forced into channels 48 until the end face 62 of beams 46 approaches or comes in contact with back wall 54 of channels 48. The distances between channel longer walls 50 and short walls 52 are slightly smaller than the distances between beam sidewalls 56 and short walls 58 and, thus, when end portions 60 of beams 46 are received within channels 48, the channel inner walls frictionally engage the walls of beams 46 and effectively retain the end portion 60 of beams 46 without any need for additional fasteners or adhesives. It is noted that when assembled, the sensor bar longer side walls 56 are generally vertically situated for added stability over longer lengths.

Connecting boots 44 further include a support portion 64 integrally formed therewith. Support portion 64 includes upper flat surface 66 and lower flat surface 68. A hole or bore 70 extends through portion 64 from surface 66 to surface 68. Support portion 64 aids in stabilizing connecting boots 44 and, as more fully described hereinbelow, provides a means by which connecting boots 44 can be hung below table 14.

The sensor bar 42 is hung below table 14 in a manner whereby sensor bar 42 is allowed to move both horizontally and vertically upwardly with respect to table 14. In this regard, eyelet member 72 having a threaded end 74 is provided and threaded end 74 is received through hole 70. A nut 76 is threadingly received on threaded end 74 thereby securing eyelet 72 onto support portion 64 of connecting boot 44. A chain link 78 extends through the eye of eyelet 72 and through a second eyelet member 80 connected to the underside of table 14. Second eyelet 80 is affixed to the underside of table 14 by welding or other suitable means. As can now be seen, the connection between table 14 and sensor bar 42 is flexible in the sense that sensor bar 42 is allowed to move both horizontally and vertically upwardly with respect to table 14. Additionally, a connection of this character is provided at each connecting boot and thus at each corner of the lift table 14. It is further noted that this flexible connection can include a plurality of links 78 and/or other flexible elongate members such as rope, rubber, etc.

As can now be appreciated, as table 14 moves downwardly, if an obstruction is encountered, the weight of sensor bar 42 which is generally light, will be overcome and the sensor bar 42 will be caused to move upwardly toward table 14. So as to provide a stop signal to the control circuit (not shown) of lift table 10, in the event that an obstruction is encountered, one or more electronic contact switches 82 are retained on sensor bar 42 and are adapted to be actuated by contacting table 14 when sensor bar 42 moves toward table 14. More specifically, contact switch 82 includes an exterior arm 84 which when depressed, causes contact switch 82 to either open or close. Contact switch 82 is also connected via wires 86 to the control circuit of lift table 10. In this fashion, when switch arm 84 is depressed, an electronic signal is created through wires 86 indicating an obstruction condition and causing the lift mechanism 16 to stop. A contact wall 88 is affixed to apron 20 and cooperates with contact arm 84 for actuating switch 82. More specifically, wall 88 is adapted to be contacted by arm 84 in the event that sensor bar 42 moves upwardly toward table 14.

Figure 5:
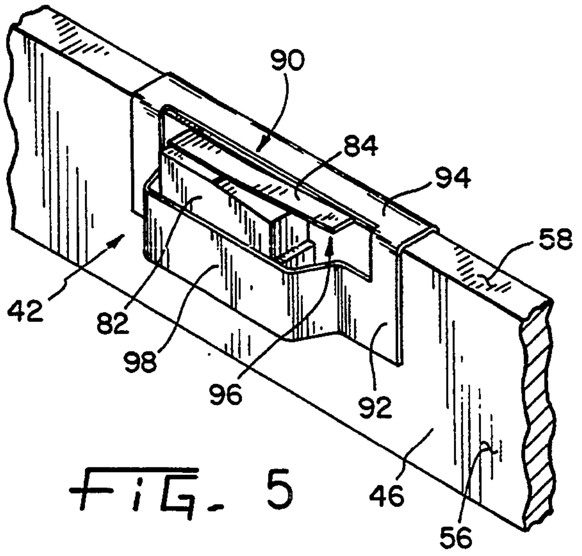
FIG. 5 is a perspective view of a part of a sensor bar, a switch clip and contact switch according to the present invention; and, FIG. 6 is an end view of the sensor bar and contact switch shown in FIG. 5.
Figure 6:
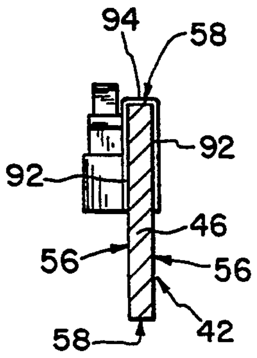

Contact switch 82 is retained on beam 46 of sensor bar 42 through the use of a switch clip 90. Switch clip 90 is made by stamping and bending processes and includes walls 92 connected together via connecting portion 94. Walls 92 and connecting portion 94 together form a U-shape and walls 92 sandwich and frictionally engage beam 46 of sensor bar 42. Thus, switch clip 90 is attached to beam 46 by merely slipping walls 92 thereover and down in position as shown in FIGS. 5 and 6.

On one of walls 92, switch clip 90 includes an opening 96 leading to a pocket 98. As best shown in FIG. 5, pocket 98 is formed by bending a portion of wall 92 and providing a gap between wall 92 and side wall 56 of beam 46. Pocket 98 is sized just slightly smaller than the width of contact switch 82 and, therefore, contact switch 82 is frictionally retained within pocket 98 and between the bent portion of wall 92 and side wall 56 of beam 46.

As can now be appreciated, the construction of the obstruction sensing guard, according to the present invention, reduces costs of manufacturing while providing reliable sensing. The flexible connections including eyelets 72 and 80 and link 78, allow the sensor bar to move both horizontally and vertically upwardly and generally prevent the potential binding of sensor bar 42 due to a horizontal force. The assembly using connecting boots 44 and variable lengths of beams 46 decreases inventory and costs of components while providing for easier construction of sensor bars for various different size lift tables. Additionally, the time necessary for assembly of the sensor bar is generally decreased and therefore the cost of assembly is also decreased. Further yet, the utilization of a switch clip for retaining the contact switch 82 in position provides versatility in allowing the placement of the contact switch or switches anywhere along the sensor bar beam 46 while making the assembly thereof substantially easy, reliable, and quick.

While the invention has been described as having specific embodiments, it will be understood that it is capable of further modification. This application is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. An obstruction sensing guard on a vertically moving table having an outer perimeter, said obstruction sensing guard comprising:

a sensor bar extending generally along and vertically below said table outer perimeter;

means for hanging said sensor bar below said table and for allowing both horizontal and vertical movement of said sensor bar with respect to said table, said hanging means including a plurality of connections between said sensor bar and said table, each of said connections comprising a flexible elongate member of a link, rope, or rubber, said members having a first end connected to said table and having a second end connected to said sensor bar; and, means for sensing movement of said sensor bar with respect to said table and interrupting movement of said table in response thereto.

2. The obstruction sensing guard of claim 1 wherein said flexible elongate members comprise a plurality of chained links.

3. The obstruction sensing guard of claim 1 wherein said table is quadrangle-shaped having four corners and wherein said sensor bar comprises connecting boots at each corner and elongate beams extending therebetween and connected to said boots.

4. The obstruction sensing guard of claim 3 wherein said second end of said flexible elongate members are connected to said boots and said flexible elongate members comprise a plurality of chained links.

5. The obstruction sensing guard of claim 1 wherein said table is quadrangle-shaped having four corners and wherein said sensor bar comprises connecting boots at each corner and elongate beams extending therebetween and connected to said boots.

6. The obstruction sensing guard of claim 1 further comprising means for engaging said sensor bar and retaining said sensing means thereon.

7. The obstruction sensing guard of claim 6 wherein said sensor means includes an electronic contact switch retained on said sensor bar with said engaging means, said contact switch being actuated by contacting said table.

8. An obstruction sensing guard on a generally horizontally disposed vertically moving quadrangle-shaped table having four corners and an outer perimeter, said obstruction sensing guard comprising:

a sensor bar extending generally along and vertically below said table outer perimeter, said sensor bar including connecting boots at each table corner and elongate beams extending therebetween and connected to said boots;

means for hanging said sensor bar below said table and for allowing movement of said sensor bar with respect to said table; and, means for sensing movement of said sensor bar with respect to said table and interrupting movement of said table in response thereto.

9. The obstruction sensing guard of claim 8 wherein said boots include beam receiving channels, each channel receiving an end portion of said beams, said channels including inner walls in frictional engagement with said beam end portions.

10. The obstruction sensing guard of claim 9 wherein said beams are rectangularly-shaped in cross section and wherein the longer sides of said rectangular shape are generally vertically situated with respect to said horizontally disposed table.

11. The obstruction sensing guard of claim 9 including a hole in each of said boots, said hanging means extending through said hole.

12. The obstruction sensing guard of claim 11 wherein said hanging means includes an eyelet member extending through said hole and affixed to said boot and a chain link extending through said eyelet member and through a second eyelet connected to said table.

13. The obstruction sensing guard of claim 9 wherein said boots are made of hard rubber.

14. The obstruction sensing guard of claim 8 including a hole in each of said boots, said hanging means extending through said hole.

15. The obstruction sensing guard of claim 14 wherein said hanging means includes an eyelet member extending through said hole and affixed to said boot and a chain link extending through said eyelet member and through a second eyelet connected to said table.

16. An obstruction sensing guard on a vertically moving table having an outer perimeter, said obstruction sensing guard comprising:

a sensor bar extending generally along and vertically below said table outer perimeter;

means for hanging said sensor bar below said table and for allowing movement of said sensor bar with respect to said table;

an electronic contact switch adapted to interrupt movement of said table when actuated; and, means for engaging said sensor bar and retaining said contact switch on said sensor bar, whereby said switch is caused to be actuated by contacting said table when said sensor bar moves toward said table.

17. The obstruction sensing guard of claim 16 wherein said engaging means includes two walls sandwiching said sensor bar, said walls frictionally engaging said sensor bar.

18. The obstruction sensing guard of claim 17 wherein said engaging means includes a pocket, said contact switch received and retained within said pocket.

19. The obstruction sensing guard of claim 17 wherein said sensor bar includes a beam having a rectangular shape in cross section and wherein said walls frictionally engage the longer sides of said rectangular shape.

20. The obstruction sensing guard of claim 16 wherein said hanging means includes a plurality of connections between said sensor bar and said table, each of said connections comprising a flexible elongate member having a first end connected to said table and having a second end connected to said sensor bar and further wherein said table is quadrangle-shaped having four corners and said sensor bar comprises connecting boots at each corner and elongate beams extending therebetween and connected to said boots.

* * * * *